United States Patent [19]

Kikuchi et al.

[11] Patent Number: 4,969,170
[45] Date of Patent: Nov. 6, 1990

[54] COLLISION PREVENTIVE DEVICE FOR MEDICAL EQUIPMENT

[75] Inventors: Hiroshi Kikuchi; Haruyoshi Otani, both of Amagasaki, Japan

[73] Assignee: Mitsubishi Denki Kabushiki Kaisha, Japan

[21] Appl. No.: 412,477

[22] Filed: Sep. 26, 1989

[30] Foreign Application Priority Data

Sep. 26, 1988 [JP] Japan ................... 63-239011

[51] Int. Cl.⁵ .............................. H05G 1/08
[52] U.S. Cl. ........................ 378/91; 378/95; 378/114; 378/117; 378/145
[58] Field of Search ............. 378/50, 65, 91, 94, 378/95, 114, 117, 145, 147

[56] References Cited

U.S. PATENT DOCUMENTS

| | | | |
|---|---|---|---|
| 4,027,156 | 5/1977 | Robinet | 378/117 |
| 4,127,775 | 11/1978 | Ohlson | 378/91 |
| 4,188,540 | 2/1980 | Reiniger | 378/91 |
| 4,648,107 | 3/1987 | Latter | 378/50 |
| 4,733,408 | 3/1988 | Beikuefner et al. | 378/117 |

FOREIGN PATENT DOCUMENTS 63-209669 8/1988 Japan .
63-209670 8/1988 Japan .
64-27568 1/1989 Japan .

OTHER PUBLICATIONS

"Safety of Medical Electrical Equipment".

Primary Examiner—Janice A. Howell
Assistant Examiner—Kim-Kwok Chu
Attorney, Agent, or Firm—Leydig, Voit & Mayer

[57] ABSTRACT

A collision preventive device for medical equipment (such as readiotherapy equipment) having moving parts to which accessaries are disengageably attached includes a contact detection circuit in which the normally closed contact detector switches disposed on the moving part and on the accessary are all coupled in series, so that an occurrence of contact of the moving part or of the accessary attached thereto can be detected by a relay coupled across a current source in series with the contact detector switches. The detector switch on the moving part and that on the accessary are coupled via a connector of a special structure: the connector half disposed on the moving part to which the accessary is attached includes a pair of terminals and a short circuit plate which is automatically electrically coupled across and disconnected from the two terminals according as the accessary is attached to or detached from the moving part, so as to couple or remove the mating connector half disposed on the accessary to or from the connector half on the moving part. Thus, irrespective of whether the accessary is attached or not, the contact detector switches that are currently utilized in detection are automatically coupled in series with the relay coupled across the current source. Further, the detection of the attachment of an accessary can be effected by a simple circuit coupled to the short circuit plate.

7 Claims, 6 Drawing Sheets

COLLISION PREVENTIVE DEVICE FOR MEDICAL EQUIPMENT

BACKGROUND OF THE INVENTION

This invention relates to collision preventive devices which, being provided in medical equipment having moving parts, furnish protection against mechanical hazards that may arise from collisions of the moving parts with the patient or other parts of the equipment; more particularly, it relates to collision preventive devices adapted to be used in such type of medical equipment that comprises moving parts to which accessary parts may be attached.

Figure 1:
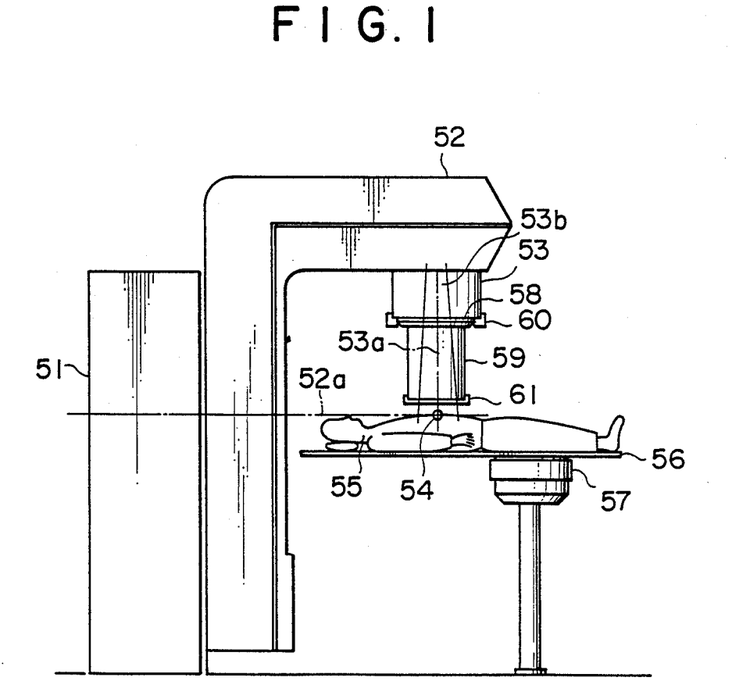
FIG. 1 shows a side view of a therapeutic linear accelerator as an example of the medical equipment having moving parts to which accessaries may be disengageably attached.

Referring to FIG. 1 of the drawings, let us first describe, as an example of medical equipment having moving parts to which accessary parts may be attached, a therapeutic linear accelerator. To a fixed support 51 is mounted a rotatable gantry 52, which rotates around the rotational axis 52a. Further, a collimator head 53, mounted on the rotatable frame 52, rotates with respect thereto around the axis 53a, to limit the field 53b of radiation generated within and emitted from the linear accelerator. The rotation axis of the collimator head 53 constitutes the central axis of the flux of radiation 53b. The point of intersection 54 of the two rotational axes 52a and 53a constitutes a central point of therapy, called an isocenter. The patient 55 under radiation therapy lies on a table top 56, whose position is determined by means of a table 57. At the attachment location 58 for accessary parts at the bottom of the collimator head 53 may be attached an accessary, such as an electron beam applicator 59 utilized in the radation therapy, as illustrated in the figure; accessaries which may be attached to the attachment location 58 of the collimator head 53 instead of the applicator 59 include a shadow tray, hollow out mechanism, and a wedge filter. In the following, the applicator 59 is taken as an example of the accessary attached to the attachment location 58 of the collimator head 53.

Figure 2A:
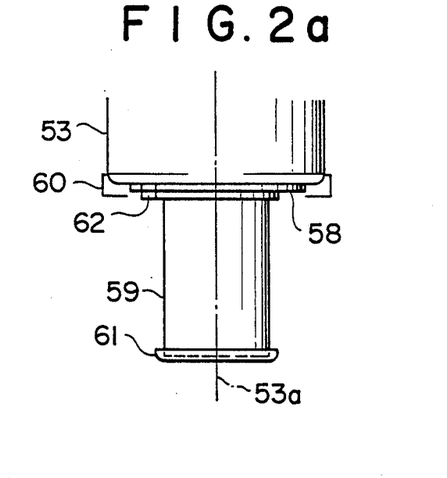
FIG. 2a shows an enlarged partial side view of the moving part (collimiator head) with an attached accessary (electron beam applicator)

In operation, the rotatable gantry 52 is rotated around its axis 52a according to the therapy program for the patient 54. Hence, the movement of the moving parts of the equipment and that of the accessary attached thereto may cause mechanical hazards. Thus, generally, medical equipment such as the above radiation therapy equipment having moving parts comprises contact detectors for detecting the contacts of the moving parts (or the accessary attached thereto) with the patient or other parts of the equipment, so that mechanical hazards arising from collisions of the moving parts or of the accessary attached thereto with the patient, etc., may be prevented. Thus, the medical equipment shown in FIG. 1 comprises contact detectors 60 and 61 provided on the collimator head 53 and the applicator 59, respectively. The detection and prevention of the collisions of the moving parts or the attached accessary may be effected by means of these contact detectors 60 and 61 with the help of a contact detection circuit of the collision preventive device shown in FIG. 2, which is disclosed in Japanese laid-open Pat. application No. 62-40182. The organization and method of operation of the collision preventive device of FIG. 2 is as follows.

Figure 2B:
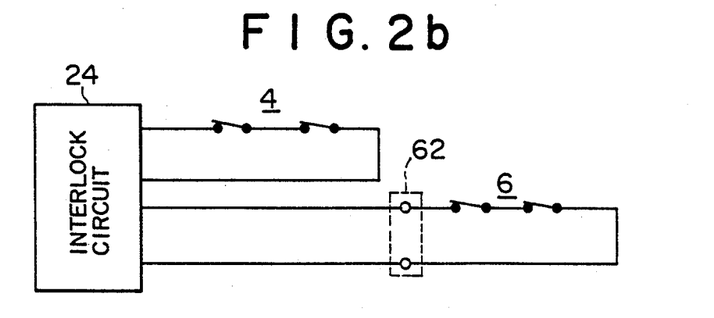
Figure 2C:
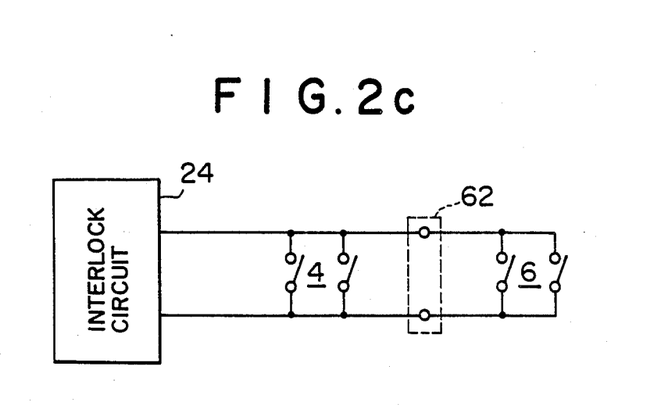

FIGS. 2b and 2c show two alternative forms of the conventional contact detection circuit, whereby the switchs 4 and 6 operated by the contact detectors 60 and 61 (shown in detail in FIG. 2a) are coupled to the interlock circuit 24 for stopping the movement of the moving parts of the medical equipment, etc. In both figures, the reference numeral 4 represents switches operated by the contact detector 60 on the collimator head 53; the reference numeral 6 represents those operated by the contact detector 61 on the applicator 59.

In the case of the circuit of FIG. 2b, the switches 4 and 6 are normally closed and are opened, respectively, when the respective contact detectors 60 and 61 come into contact with an object. The serially connected switches 4 operated by the contact detector 60 and the serially connected switches 6 operated by the contact detector 61 are coupled to the interlock circuit 24 via independent serial circuits; thus, the switches 6 of the detector 61 are connected directly to the interlock circuit 24 via the connector 62. Hence, when the detectors 60 and 61 come into contact with an object to open at least one of the switches 4 and 6 the interlock circuit 24 activates a control sequence for stopping the movement of the moving parts of, or the generation of radiation within, the medical equipment.

In the case of the circuit of FIG. 2c, on the other hand, the switches 4 and 6 are normally open and are closed respectively when the contact detectors 60 and 61 come into contact with an object. The parallel switches 4 operated by the contact detector 60 and the parallel switches 6 operated by the contact detector 61 are coupled in parallel via a connector 62, so as to be coupled together, in parallel circuit relationship, to the interlock circuit 24. Thus, when the detector 60 or 61 comes into contact with an object, to close at least one of the switches 4 or 6, the interlock circuit 24 senses an occurance of such contact by the closure of the circuit and activates a sequence for stopping the movement of the moving parts of, or the generation of radiation within, the medical equipment.

The contact detection circuit shown in FIGS. 2b and 2c, however, have the following disadvantages. In the case of the contact detection circuit of FIG. 2b, the state in which the applicator 59 (an accessary) is not attached and the state in which an occurance of contact of the applicator 59 takes place are identical; hence, means for detecting the attachment of an accessary is indispensable. Further, two independent sensing means for detecting the opening of the switches 4 and 6 must be provided. As a result, the organization of the contact detection circuit becomes complicated. On the other hand, the contact detection circuit of FIG. 2c becomes incapable of contact detection, if there is an electrical disconnection along the circuit; this may present a grave danger if such electrical disconnection, which may occur at the connector 62 or along the wiring of the circuit, is not discovered. In addition, since the states in which the applicator 59 is properly attached and in which it is not attached cannot be distinguished, a further detecting means for detecting the proper attachment of accessaries is generally necessary or at least desirable. This accessary attachment detecting means must be implemented in the form of a separate circuit, and thus entails a substantial complication of the overall organization of the detection circuit.

SUMMARY OF THE INVENTION

The primary object of this invention is therefore to provide a collision preventive device for medical equipment which comprises moving parts to which accessaries are disengageably attached, wherein the contact detection circuit of the collision preventive device is simple in organization and reliable in operation.

A more particular object of this invention is to provide such a collision preventive device in which the detection of an occurence of contact of the moving parts and of the accessary attached thereto can be effected by means of a single detection circuit of serially connected contact detecctor switches (so that the circuit organization is simplified while its reliability is enhanced), and, at the same time, the attachment or detachment of the accessary does not require a special operation other than that of simple attachment of detachment.

Additional object of this invention is to provide such a collision preventive device in which the detection of the attachment of an accessary to the moving parts of the medical equipment can be effected by means of a simple circuit.

The above objects are accomplished in accordance with the principle of this invention in a collision preventive device for the above type of medical equipment wherein the contact detection circuit of the collision preventive device is provided with a connector of a special structure for connecting the contact detector switches disposed on the moving part and those on the accessary. Namely, the connector half disposed on the moving part, which is coupled in series with at least one normally closed contact detector switch disposed on the moving part and a current detecto (e.g. and electric relay) coupled across a current source, includes a pair of terminals and a short circuit plate electrically disconnectably coupled thereacross, wherein the short circuit plate is kept in electrical contact with the terminals by an action of an urging means when the accessary is not attached. Thus, when the accesary is not attached, the contact detector switch on the moving part, the current detector, and the short circuit plate are coupled acoss the current source. On the other hand, the mating connector half disposed on the accessary, which includes a pair of terminals across which at least one normally closed contact detector switch disposed on the accessary is coupled, comprises disconnection means which automatically electrically disconnects the short circuit plate from the terminals of the connector half disposed on the moving part, when the accessary is attached to the moving part and the two connector halves are coupled to each other. Thus, when the accessary is attached to the moving part of the medical equipment, the normally closed contact detector switche disposed on the moving part and that disposed on the accessary attached thereto are coupled in series with the current detector (e.g. an electric relay) coupled across the current source. The normally closed contact detector switches on the moving part and on the accessary are both opened in response to an occurrence of contact of the moving part and accessary, respectively. Thus, irrespective of whether the accessary is attached to the moving part or not, the current detector can detect an occurence of contact by an absence of current flowing therethrough.

In a preferred form, the connector may have the following organization: the terminals of the connector half on the moving part are rendered capable of movement with respect to fixed short circuit plate, and the urging and disconnection means force these terminals into and out of the position of electrical contact with the short circuit plate.

By means of the above connector, the contact detector switches that are utilized in detection can be automatically coupled in series with the current detector by simple operations of attachment and detachment of an accessary. Further, if an electrical disconnection occurs along the contact detection circuit, such disconnection has the same effect as a detection of an occurence of contact of the moving part or of the accessary, and stops the operations of the medical equipment; hence, the reliability of the detection circuit is enhanced.

In the case where the detection of the attachment of an accessary is desired, such detection can be effected by a simple circuit coupled to the short circuit plate of the connector half on the moving part. Further, in the case where an additional accessary is disengageably attached to the accessary directly attached to the moving part, a connector having a structure identical to the above may be utilized to connect serially the normally closed contact detector switches disposed on the two accessaries, respectively.

The novel features which are believed to be characteristic of this invention are set forth with particularlity in the appended claims. This invention itself, however, both as to its organization and method of operation, together with further objects and advantages thereof, may best be understood from the following detailed description of the preferred embodiments, taken in connection with the accompanying drawings.

BRIEF DESCRIPTION OF THE DRAWINGS

FIG. 2a through 2c show a collision preventive device which may be installed in the medical equipment of FIG. 1, wherein FIG. 2a and 2b show conventional contact detection circuits of the collision preventive device;

FIG. 3 shows a contact detection circuit of the collision preventive device according to this invention, wherein FIG. 3a shows the contact detection circuit in the state where an accessary is not attached to the moving part, while

FIG. 4 shows the structure of the connector of the contact detection circuit of FIG. 3, wherein

In the drawings, like reference numerals represent like or corresponding parts.

DETAILED DESCRIPTION OF THE PREFERRED EMBODIMENTS

Referring to FIGS. 3 through 6 of the drawings, embodiments of this invention are described. First, let us describe a first embodiment referring to FIGS. 3 and 4.

Figure 3A:
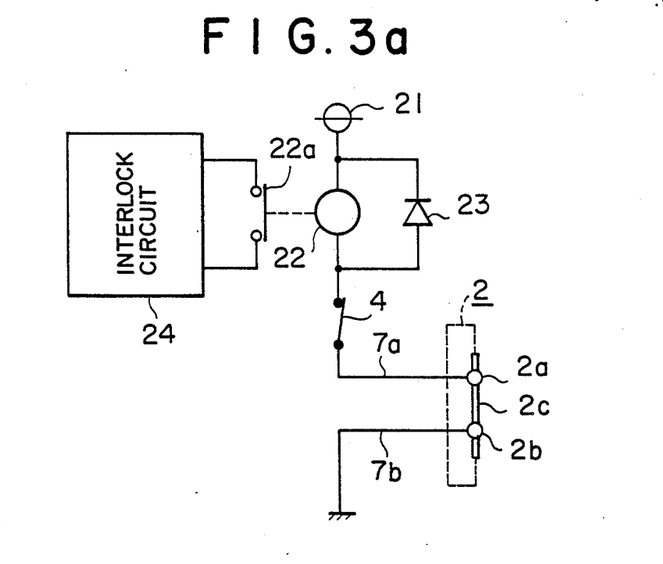
Figure 3B:
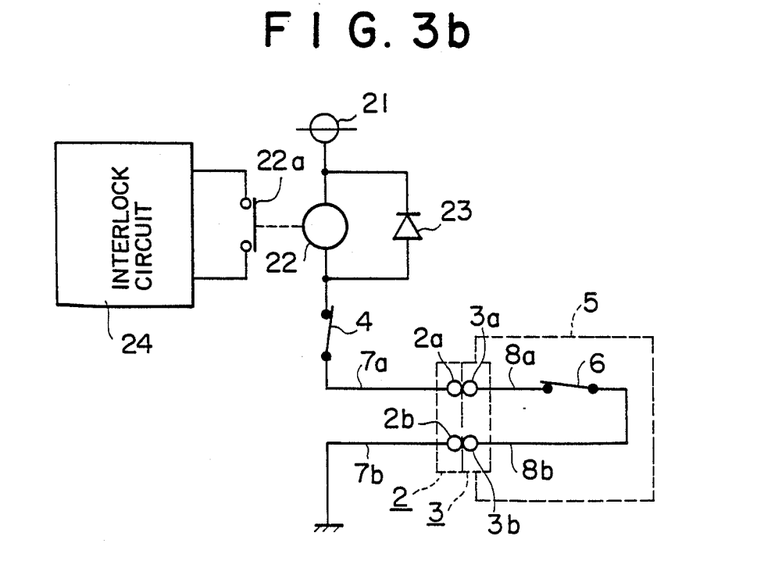
FIG. 3b shows the circuit in the state where an accessary is attached thereto.

FIG. 3a shows a contact detection circuit of a collision preventive device for medical equipment having moving parts to which an accessary may be disengageably attached; the following description is made in the case where the circuit is installed in the medical equipment shown in FIG. 1. FIG. 3b shows the same circuit in the state where an accessary 5, such as an electron beam applicator 59, is attached to the collimator head 53. As shown in FIG. 3a, across a power or current source 21 and ground is coupled a serial circuit which comprises the following elements: an electric relay 22 having a relay contact 22a and provided with a protective diode 23 coupled in anti-parallel relationship therewith to prevent the oppositely directed current to flow through the coil of the relay 22; a normally closed switch 4 opened by the contact detector 60 (see FIG. 1) when the detector 60 comes into contact with an object; and a connector half 2 having terminals 2a and 2b coupled via wiring 7a and 7b to the switch 4 and ground, respectively, and a short circuiting plate 2c which couples (i.e. short-circuits) the terminals 2a and 2b of the connector half 2 when an accessary 5 such as an electron beam applicator is not attached. When, however, the connector half 3 of an accessary 5 is coupled thereto as shown in FIG. 3b, the short circuiting plate 2c is automatically disconnected from the terminals 2a and 2b. The mechanism of this automatic electrical disconnection of the short circuit plate 2c from the terminals 2a and 2c will be described in detail below referring to FIG. 4. The relay 22 keeps the contact 22a closed when it is supplied with a voltage. The interlock circuit 24 activates a sequence for stopping the operations, such as the movement of of the moving parts, of the medical equipment, when the contact 22a of the relay is opened.

On the other hand, the contact detection circuit of the accessary 5 comprises the following: a connector half 3 having two terminals 3a and 3b, which is disengageably coupled with the connector half 2 disposed on the moving part such as the collimator head 53 of the medical equipment; and a normally closed switch 6 (which is operated by a contact detector such as that shown at reference numeral 61 in FIG. 1) coupled across the two terminals 3a and 3b of the connector half 3 via wiring 8a and 8b. As pointed out above and described in detail below, the short circuiting plate 2c (not shown in FIG. 3b) is electrically disconnected from the contacts 2a and 2b when the accessary 5 is attached; thus, when the accessary 5 is attached, the switch 6 operated by the contact detector on the accessary 5 is coupled in series with the relay 22 and the switch 4 operated by the contact detector on the moving part of the main body of the medical equipment.

The method of operation of the contact detection circuit described above is now easy to comprehend. In the state shown in FIG. 3a, the serial circuit of the relay 22, the switch 4, and the short circuiting plate 2c of the connector half 2 is coupled across the current source 21 and the ground; thus, the relay 22 is normally supplied with a current therethrough, and hence keeps the contact 22a closed. During the time when the contact 22a is closed, the interlock circuit 24 allows the normal operation of the medical equipment, such as the rotational movement of the rotatable gantry 52 or the generation and emission of the radiation. When, however, the contact detector 60 (see FIG. 1) on the moving part of the medical equipment comes into contact with an object to open the switch 4, the supply of current to the relay 22 is stopped; hence, the contact 22a is opened, and, in response thereto, the interlock circuit 24 immediately stops the operations (such as the movement of the moving parts or the generation of the radiation) of the medical equipment. On the other hand, in the state shown in FIG. 3b, the switch 6 (which is opended when the contact detector 61 on the accessary comes into contact with an object), as well as the switch 4, is coupled in series with the relay 22; thus, either one of the contact detectors 60 and 61 comes into contact with an object to open at least one of the switches 4 and 6, the supply of current to the relay 22 is stopped and, accordingly, the interlock circuit 24 stops the operations of the medical equipment in the same manner as described above.

In the above contact detection circuit, the contact detectors 60 and 61 on the moving part (collimator head) 53 and the accessary 5 (applicator 59) are each provided with a single switch 4 and 6. The contact detectors 60 and 61, however, may each comprise a plurality of switches which are operated by the respective contact detectors. In such case, those switches corresponding to the switches 4 and 6 should all be normally closed and should all be coupled in series circuit, so that when at least one of those switches are opened by the operation of the contact detectors, the current supply to the relay 22 is stopped. Further, it is noted that the supply of current to the relay 22 is stopped as well in the case when a failure occurs at any one place along the serial circuit comprising the relay 22 and coupled across the current source 21 and the ground; for example, the current supply to the relay 22 is stopped by a failure of the voltage source 21, the disconnection of the wiring 7a, 7b, 8a, and 8b, or the mal-contact of the terminals between the connector halves 2 and 3. If such a failure takes place in the contact detection circuit, the interlock circuit 24 automatically stops the operations of the medical equipment; this furnishes a fail-safe function for the contact detection circuit according to this invention.

Figure 4A:
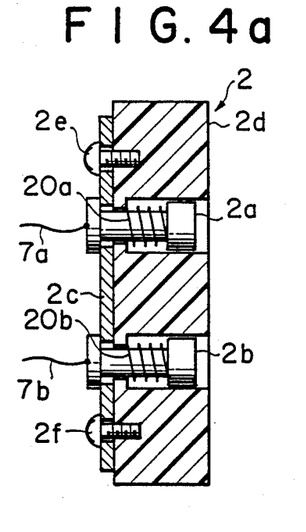
FIG. 4a shows a side sectional view of the connector half on the moving part in the state where the accessary is not attached.

As pointed out above, the connector half 2 of the contact detection circuit includes a short circuit plate 2c which is automatically disconnected from the terminals 2a and 2b when the mating half 3 is connnected thereto. Referring to FIG. 4 of the drawings, let us now describe the structure and the method of operation of these connector halves 2 and 3 in detail. The state of the connector half 2 in which it is not mated with the other half 3 is shown in FIG. 4a. Thus, the connector half 2 comprises a rectangular block 2d of an electrically insulating material; the electrically conducting short circuit plate 2c is fixedlly secured on the outer main surface of the block 2d via a pair of fixing screws 2e and 2f. Through the direction of thickness of the block 2d and the plate 2c are formed in axial alignement a pair of throughholes through which the cylindrcial terminals 2a and 2b, having radially enlarged end disks connected by respective intermediate column portions, extend, so as to be slidable in their axial direction, wherein the top end disks (at the left in the figure) and the intermediate column portion of the terminals 2a and 2b have a diameter greater and smaller, respectively, than that of the holes formed in the plate 2c, and the top end portions of the terminals being positioned outside of the plate 2c. The through-holes in the block 2d have a radially inwardly extending annular extension at the outer end thereof (at the left side in the figure) whose inner diameter is smaller than that of the bottom end disks of the terminals 2a and 2b; helical urging springs 20a and 20b, disposed around the intermediate column portion of the terminals 2a and 2b and bearing on these extensions of the through-holes in the block 2d at its left end in the figure and on the bottom end disks of the terminals 2a and 2b at its right end in the figure, urge the respective terminals 2a and 2b toward right in the figure with respect to the block 2d; thus, when the mating half 3 is not connected to the contact half 2, the outer end disks of the terminals 2a and 2b, coupled to the the wires 7a and 7b, respectively, are forced into a position of contact with the short circuit plate 1.

Figure 4B:
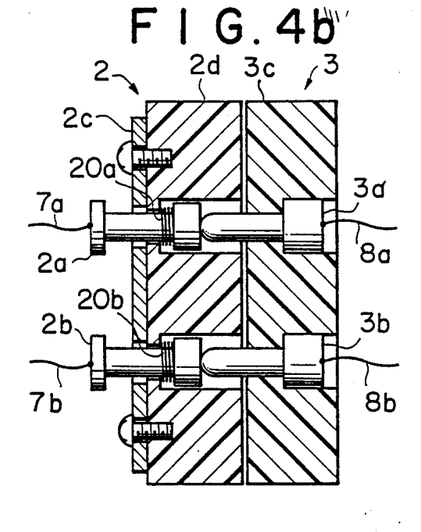
FIG. 4b and 4c show a sectional side view and a perspective view, respectively, of the connector halves on the moving part and on the accessary in the coupled state.
Figure 4C:
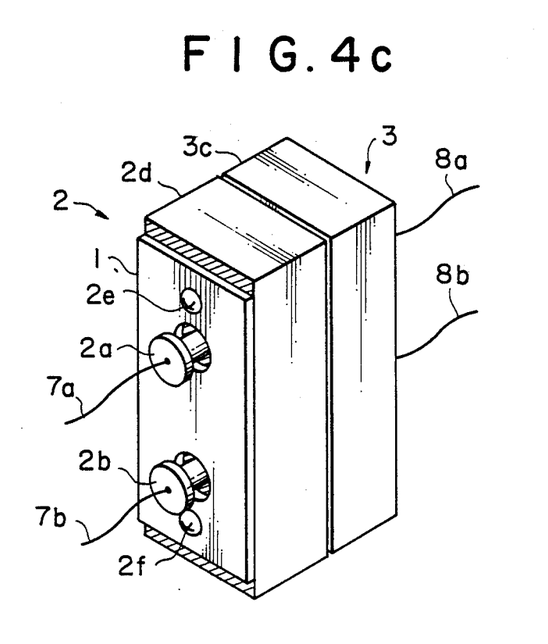

On the other hand, as shown in FIG. 4b, the contact half 3 comprises a rectangular block 3c of an electrically insulating material, and a pair of terminals 3a and 3b positioned in axial alignment with the terminals 2a and 2b of the connector half 2 and having enlarged base portions (at the right side in the figure) and cylindrical top column portions extending from the respective base portions; the terminals 3a and 3b are fixedly secured to the block 3c at the base portion (which are coupled to the wires 8a and 8b, respectively) and partially at the top cylindrical portion thereof, wherein the respective extreme top portions (the left-most portion in the figure) of a predetermined height extend outward from the mating surface of the block 3c. Thus, when the connector halves 2 and 3 are coupled with each other as shown in FIG. 4b and 4c, the top outward extensions of the terminals 3a and 3b abut on the bottom end disks of the terminals 2a and 2b, respectively, to force and move them in the axial direction against the urging force of the springs 20a and 20b into a position at which the top disks of the terminals 2a and 2b are displaced and electrically disconnected from the short circuit plate 2c. (it should be noted that the diameter of the intermediate column portions of the terminals 2a and 2b is smaller than that of the holes in the plate 2c, so that these intermediate column portions of the terminals 2a and 2b are separated by a gap from the plate 2c.) As a result, when the accessary 5 is attached to the moving part (e.g. collimator head 53) of the medical equipment to couple the contact halves 2 and 3 together, the short circuit plate 2c is automatically electrically disconnected from the terminals 2a and 2b; on the other hand, when the accessary 5 is detached, the terminals 2a and 2b automatically return to their original positions thanks to the urging force of the springs 20a and 20b. Thus, as described above, the short circuit plate 2c of the connector is automatically connected and disconnected from the terminals 2a and 2b of the connector half 2 by simply attaching and detaching the accessary 5 to the moving part of the electrical equipment.

Figure 5:
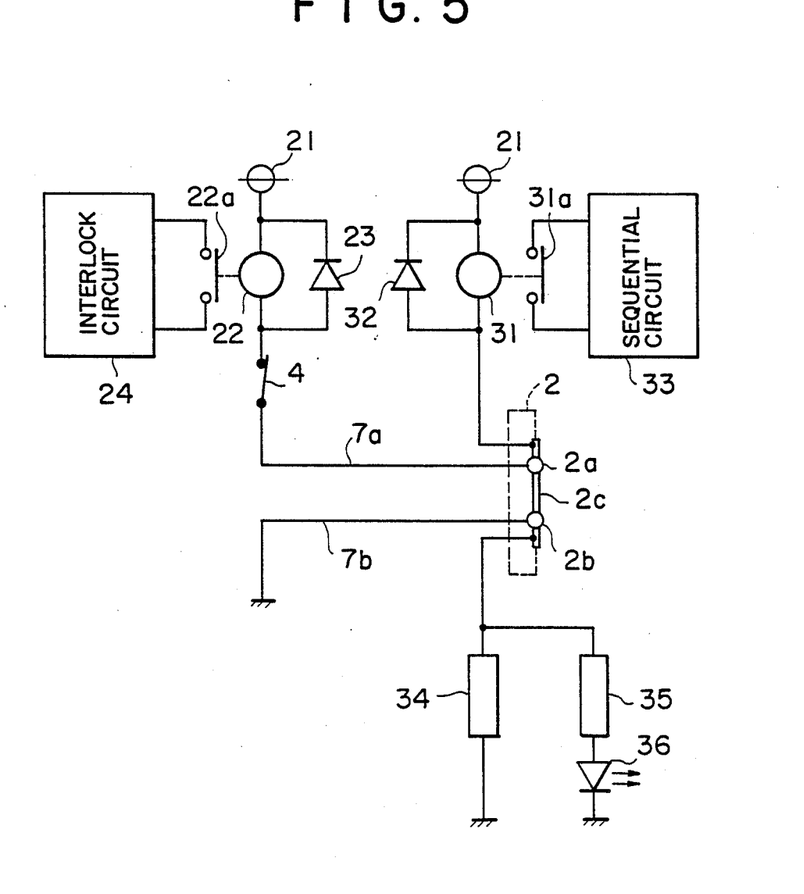
FIG. 5 shows a modification of the circuit of FIG. 3, wherein an accessary attachment detection circuit is coupled to the short circuit plate of the connector half disposed on the moving part.

By the way, it may sometimes be neccessary to detect and display the attachment of an accessary. Thus, FIG. 5 shows a modification of the above embodiment in which a further circuit is provided for detecting and displaying the attachment of an accessary, wherein the detection of the attachment of an accessary can be effected by a simple circuit utilizing the short circuit plate 2c of the connector half 2. In FIG. 5, the elements (shown in the left half of the figure) of the contact dectection circuit, including the connector half 2, have structures similar to those of the corresponding elements of the circuit of FIG. 3a designated by the same reference numerals, respectively; the attachment detection circuit, on the other hand, is constituted as follows: An electric relay 31, having a relay contact 31 and provided with a protective diode 32 coupled in anti-parallel relationship therewith, is coupled across a current source 21 and an end of the short circuit plate 2c of the connector half 2. The relay contact 31a makes and closes the circuit coupled to a sequential circuit 33, so that the sequential circuit 33 can recognize the state of the relay 31. Further, a resistor 34 and a serial circuit of a resistor 35 and a light-emitting diode 36 are coupled across another end of the short circuit plate 2c and the ground. The connector half 2 of the contact detection circuit and the mating half 3 (not shown in FIG. 5) of an accessary have the same structures as described above. Thus, it is noted that the the serial circuit including the relay 31, the short circuit plate 2c, and the parallel connection of the resistor 34 and the series of resistor 35 and the light emitting diode 36 is electrically connected to or disconnected from the terminals 2a and 2b according as an accessary (such as that referenced by numeral 5 in FIG. 3b) is attached to or detached from the moving part of the electrical equipment.

The method of operation of the above attachment detection circuit is as follows. In the state (shown in FIG. 5) in which an accesary is not attached, the short circuit plate 2c is grounded via the terminal 2b of the connector half 2 and the wiring 7b. Thus, the relay 31 of the attachment detection circuit is supplied with a voltage thereacross and a current flows therethrough; the relay 31 is thus operated and the sequential circuit 33 senses via the operated relay contact 31a that an accessary is not attached. When this is the case, the sequential circuit 33 may output a corresponding signal (representing that an accessary is not attached) to the interlock circuit, or a therapy recorder or a remote control device (not shown) of the medical equipment in which it may be utilized in the display, etc.

On the other hand, as described above, the short circuit plate 2c is electrically disconnected from the terminals 2a and 2b of the connector half 2 when an accessary is attached to the moving part of the electrical equipment (see FIGS. 3 and 4); hence, when an accessary is attached, the voltage across the source 21 and the ground is applied across the serial connection of the relay 31 and the parallel circuit consisting of the resistor 34 and the serially connected resistor 35 and diode 36. In the design of the attachment detection circuit, by the way, the resistance values of the resistors 34 and 35 are selected sufficiently great such that the relay 31 stops to be energized under this condition; thus, the sequential circuit 33 senses, from the face that relay contact 31a is not operated by the relay 31, that an accessary is properly attached. On the other hand, the light emitting diode 36 receives enough current from the source 21 via the resistor 35 and the relay 31, so as to emit light, thereby display the attachment of an accessary.

The attachment detection circuit is effective in preventing the following danger: if the accessary 5 (refer to FIG. 3b) is not properly attached and the short circuit plate 2c is not electrically disconnected from the terminals 2a and 2b of the connector half 2, the opening of the switch 6, which indicates an occurrance of contact of the accessary 5 with an object, cannot be detected by the relay 22 of the contact detection circuit. To prevent this danger, the attachment detection circuit of FIG. 5 can detect and display whether the accessary is properly attached and the short circuit plate 2c is electrically disconnected from the terminals 2a and 2b. Incidentally, it is noted that usually, the kind of the accessary 5 (e.g. whether it is an electron beam applicator, a shadow tray, a wedge filter, a punch devcie, etc.) is represented by an accessary type recognition signal which is transmitted via a special terminal provided in the connector halves 2 and 3 as described above, in addition to the terminals 2a, 2b, 3a, and 3b for transmitting the contact detection signal; however, even in the case where such a recognition signal for representing the kind of the accessary is provided, the sequential control of the equipment can be effected in such manner that the operations of the equipment is stopped when the attachment of an accessary is not detected by means of the relay 31. Thus, in summary of the above, it is pointed out that the signal representing the attachment and detachment of an accessary is obtained by a simple circuit utilizing the short circuit plate 2c according to this invention.

Figure 6:
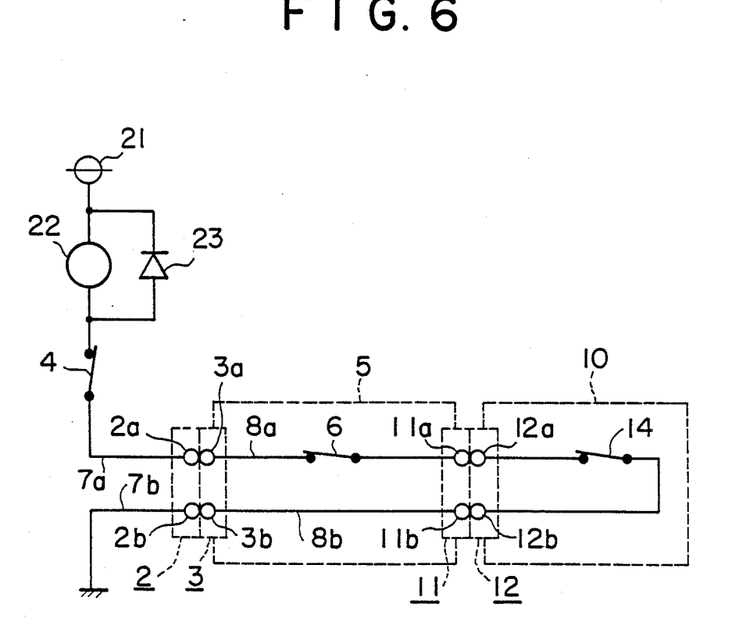
FIG. 6 shows another modification of the circuit of FIG. 3, wherein an additional accessary may be disengageably attached to the accessary directly attached to the moving part of the medical equipment.

By the way, in the case of the accessary of FIG. 3b, a single accessary 5 is attached to the moving part of the medical equipment. However, it may sometimes be desirable to attach an additional accessary to the one already attached to the moving part of the medical equipment. Thus, FIG. 6 shows the contact detection circuit according to this invention in such case, wherein an additional accessary 10 is attached to the accessary 5. The accessaries 5 and 10 comprise respective connector halves 11 and 12 for their mutual connection, which connector halves have structures similar to those of the connector halves 2 and 3, respectively, which have been described in detail above by reference to FIG. 4. Namely, the connector half 11, having a pair of terminals 11a and 11b and a short circuit plate (not shown) electrically disconnectably connector half 2 shown in FIGS. 4a through 4c; the connector half 12 has a structure similar to that of the connector half 3 shown in the same figures. Thus, when the accessary 10 is attached to the accessary 5, a normally closed switch 14, which is opened when the contact detector of the accessary 10 comes into contact with an object, is coupled in series with switches 4 and 6 of the contact detection circuit. Consequently, when at least one of the switches 4, 6, and 14 is opened, the supply of current to the relay 22 is stopped and an occurrence of a contact is detected. Otherwise, the operation is similar to the case described above.

While description has been made of the particular embodiments of this invention, it will be understood that many modifications may be made without departing from the spirit of this invention. For example, the relays 22 and 31 may be replaced by any elements which are capable of detecting the current or voltage. Further, the light emitting diode may be replaced by an electric lamp or a liquid crystal display whose state is changed by a predetermined magnitude of the applied electric field. Further, if there is no danger of contact or collision of the moving part (e.g. the collimator haed 53) of the medical equipment, the contact detector thereof including the switch 4 may be omitted, in which case the contact detection circuit is reduced to the state of the above-described circuit in which the switch 4 is always closed. Likewise, there are accessaries which do not comprise contact detectors; even then, the accessaries may be provided with a connector half similar to the connector half 3 of FIG. 4 whose terminals, however, are short circuited, so that the attachemnt and detachment of the accessries can be detected by the attachment detection circuit of FIG. 5. Furthermore, it goes without saying that this invention is applicable to any type of medical equipment having moving parts to which accesaries may be disengageably attached, such as: radiotheraply equipement, radiography equipment, and X-ray CT (computerized tomography) equipment. The appended claims are contemplated to cover any such modifications as fall within the true spirit and scope of this invention.

What is claimed is:

1. A collision preventive device for medical equipment having at least one moving part to which at least one accessory part can be disengageably attached, said collision preventive device comprising:
   a first contact detector, disposed on the moving part of the medical equipment, including at least one normally closed switch which is opened in response to an occurrence of contact of the moving part with another object;
   a connector half disposed on the moving part and having a pair of terminals and a short circuit plate electrically disconnectably coupled thereacross to be coupled electrically in series with the switch of said first contact detector, wherein the connector half on the moving part comprises urging means for keeping said short circuit plate electrically connected across said pair of terminals during a time when an accessary part is not attached to the moving part of the medical equipment;
   current detector means, coupled in a series circuit with the switch of said first contact detector and said connector half on the moving part, for detecting a presence or absence of a current flowing therethrough;
   current source means for supplying a current across the series circuit of said first contact detector, said connector half on the moving part, and said current detector means; and
   a circuit provided within at least one accessary part which is disengageably attached to the moving part of the medical equipment, wherein said circuit provided in the accessary includes:
   a mating connector half disposed on the accessary and having a pair of terminals each of which is electrically coupled to a corresponding one of said terminals of the connector half on the moving part when the accessary is attached to the moving part, wherein said mating connector half comprises disconnection means for automatically electrically disconnecting said short circuit plate of the connector half on the moving part from the terminals thereof during a time when the accessary part is attached to the moving part of the medical equipment, so that the short circuit plate is automatically electrically disconnected from and connected to the terminals of the first connector half according as the accessary part is attached to or detached from the moving part of the electrical equipment; and
   a second contact detector disposed on the accessary part and including at least one normally closed switch which is coupled across the terminals of the mating connector half on the accessary part, so as to be coupled in series with the current detector means and the switch of the first contact detector on the moving part at a time when the accessary part is attached to the moving part, said switch of the second contact detector being opened in response to an occurance of contact, with another object, of the accessary part attached to the moving part of the medical equipment.

2. A collision preventive device as claimed in claim 1, wherein said terminals of the connector half on the moving part are capable of movement with respect to the short circuit plate that is fixed, and said urging means urges the terminals of the connector half on the moving part to a position of electrical contact with the short circuit plate, wherein said disconnection means of the mating contact half disposed on the accessary forces against an urging force of the urging means the movable terminals of the connector half on the moving part out of the position of electrical contact with the short circuit plate.

3. A collision preventive device as claimed in claim 2, wherein:
   said connector half on the moving part of the medical equipment comprises a block of an electrically insulating material to whose outside surface opposite to a mating surface said short circuit plate is fixedly secured, said block and said short circuit plate having a pair of through-holes formed in axial alignment in a direction of thickness of the block and the short circuit plate, the through-holes formed in the block each having on an inner surface thereof an annular radially inward extension at an end at said outside surface thereof;
   said pair of terminals of the connector half on the moving part, which terminals are cylindrical in form and each of which comprises a top and a bottom end disk of an enlarged diameter connected by an intermediate column of a reduced diameter, extend axially slidably through said pair of through-holes, respectively, formed through the block and the short circuit plate, wherein the top end disks having a diameter greater than a diameter of the through-holes in the short circuit plate are situated outside of the short circuit plate and the bottom end disks are accomodated axially slidably within the through-holes in the block;
   said urging means comprises a pair of helical springs each of which is disposed around the intermediate column of the respective terminals of the connector half on the moving part, to bear at one end thereof on said annular extension of the respective through-holes in the block and at the other end thereof on the bottom end disk of the respective terminals of the connector half on the moving part, the helical springs urging the terminals axially with respect to the block so as to force the top end disks of the terminals into electrical contact with the short circuit plate; and
   the mating connector half comprises a block of an electrically insulating material to which a pair of cylindrical terminals are secured to extend by a predetermined height from a mating surface of the block in axial alignement with said through-holes formed in the block of the connector half on the moving part, wherein the disconnection means of the mating connector half comprises the extensions of the predetermined height of the terminals of the mating connector half which abut on the bottom end disk of the terminals of the first connector half so as to slide them in said through-holes with respect to the block of the connector half on the moving part in a direction away from the mating surface thereof, so that the top end disks of the terminals of the connector half disposed on the moving part are moved out of electrical contact with the short circuit plate.

4. A collision preventive device as claimed in claim 1, further comprising an accessary attachment detection circuit means, coupled to said short circuit plate of the connector half disposed on the moving part, for detecting an attachment of an accessary part to the moving part of the electrical equipment.

5. A collision preventive device as claimed in claim 4, wherein said accessary attachment detection circuit means comprises:
   a second current detector means, coupled in series with the short circuit plate, for detecting a presence or absence of current flowing therethrough;
   a resistor coupled in series with the short circuit plate and the second current detector means; and
   current source means for supplying current across the serial circuit of the short circuit plate, the second current detector means, and the resistor, wherein the second current detector means detects an attachment of an accessary part in response to an absense of current flowing therethrough.

6. A collision preventive device as claimed in claim 5, further comprising display means, coupled is parallel with said resistor, for displaying an attachment of an accessary part in response to a current flowing therethrough.

7. A collision preventive device as claimed in claim 1, the device being for medical equipment having at least one moving part to which at least one accessary part may be disengageably attached directly, at least one additional accessary part being disengageably attached, in its turn, to the accessary part directly attached to the moving part of the medical equipement, wherein:
   said circuit of the collision preventive device provided in the accessary directly attached to the moving part of the medical equipment further comprises an additional connector half having a pair of terminals and a short circuit plate electrically disconnectiably coupled thereacross, said additional connector half being coupled electrically in series with said switch of said circuit provided in the accessary directly attached to the moving part;
   wherein said collision preventive device further comprises an additional circuit provided in at least one additional accessary part disengageably attached to the accessary ditectly attached to the moving part, which additional circuit includes:
   an additional mating connector half disposed on the additional accessary part and having a pair of terminals each of which is electrically coupled to a corresponding one of the terminals of the additional connector half at a time when the additional accessary is attached to the accessary part directly attached to the moving part of the medical equipement; wherein said additional contact half and said additional mating contact half have organizations identical, respectively, to those of the connector half disposed on the moving part and of the mating connector half mating therewith; and
   a third contact detector disposed on said additional accessary and including at least one normally closed switch which is coupled across the terminals of the additional mating connector half so as to be coupled in series with the switches of the first and the second contact detector at a time when the additional accessary part is attached to the accessary part directly attached to the moving part, said switch of the third contact detector being opened in response to an occurence of contact with another object of the additional accessary part.

* * * * *